United States Patent [19]

Mastrorio

[11] Patent Number: 5,762,125
[45] Date of Patent: Jun. 9, 1998

[54] CUSTOM BIOIMPLANTABLE ARTICLE

[75] Inventor: Brooke W. Mastrorio, Lakeville, Mass.

[73] Assignee: Johnson & Johnson Professional, Inc., Raynham, Mass.

[21] Appl. No.: 723,791

[22] Filed: Sep. 30, 1996

[51] Int. Cl.⁶ .................................................. B22C 7/02
[52] U.S. Cl. ........................... 164/4.1; 164/34; 164/35; 164/45; 164/516
[58] Field of Search ........................... 164/34, 35, 4.1, 164/45, 516

[56] References Cited

U.S. PATENT DOCUMENTS

| 3,835,913 | 9/1974 | Vandemark et al. | 164/35 |
|---|---|---|---|
| 4,066,116 | 1/1978 | Blazek et al. | 164/17 |
| 4,109,699 | 8/1978 | Miller et al. | 164/244 |
| 4,355,428 | 10/1982 | Deloison et al. | 3/1.91 |
| 4,600,546 | 7/1986 | Grundei | 264/59 |
| 4,651,799 | 3/1987 | Chandley | 164/35 |
| 4,730,657 | 3/1988 | Carson et al. | 164/23 |
| 4,844,144 | 7/1989 | Murphy et al. | 164/35 |
| 5,007,931 | 4/1991 | Smith | 623/23 |
| 5,069,271 | 12/1991 | Chandley et al. | 164/516 |
| 5,176,188 | 1/1993 | Quinn et al. | 164/516 |
| 5,204,055 | 4/1993 | Sachs et al. | 419/2 |
| 5,391,460 | 2/1995 | Dougherty et al. | 430/269 |

FOREIGN PATENT DOCUMENTS

| 63-194842 | 8/1988 | Japan | 164/35 |
|---|---|---|---|
| 63-212039 | 9/1988 | Japan | 164/35 |
| 360845 | 3/1991 | Japan . | |

OTHER PUBLICATIONS

*Alternative Methods for Custom Implant Production Utilizing a Combination of Rapid Prototyping Technology and Conventional Investment Casting*, B.A. Weeden, A.P. Sanders, D.S. LaSalle, G.P. Trottier, Johnson & Johnson Professional, Inc., 325 Parmount Dr., Raynham., MA 02767, Mar. 31, 1996.

Primary Examiner—Kuang Y. Lin
Attorney, Agent, or Firm—Nutter, McClennen & Fish, LLP

[57] ABSTRACT

A method of making a custom, bioimplantable article, such as a joint prosthesis component, is provided using computer aided design, rapid prototyping, and investment casting techniques. The method includes the creation of a data file, using computer aided design (CAD) techniques, that defines a negative or a shell of a portion of a bioimplantable article that is custom configured for a specific arthroplasty patient. The data file for the shell of the custom portion of the bioimplantable article is accessed by a rapid prototyping machine, such as a three-dimensional printer, to create a mold that corresponds to the shell. The mold, generally a heat-resistant ceramic, is positioned relative to an existing, non-custom representation of a bioimplantable article to define a hybrid component. A heat-resistant shell is formed around the hybrid component and the non-custom representation of a bioimplantable article is removed from the shell using heat. Molten metal is introduced into the ceramic shell and allowed to harden. The ceramic shell is removed and the resultant custom, bioimplantable article is subjected to standard surface finishing procedures as required.

19 Claims, 3 Drawing Sheets

CUSTOM BIOIMPLANTABLE ARTICLE

FIELD OF THE INVENTION

The present invention relates to fabrication of medical implants, and more particularly to custom manufacture of bioimplantable articles utilizing computer aided design and a combination of rapid prototyping technology and investment casting techniques.

BACKGROUND OF THE INVENTION

The production of custom bioimplantable articles, such as joint prosthesis components, is a costly and time consuming process. Current techniques require a specialized engineer to review a patient's x-rays and communicate with a surgeon to determine an overall implant configuration for the individual patient and to identify features or portions of the implant that must be customized. The engineer then creates hand drawings and/or solid computer assisted design (CAD) models of a custom implant configuration. A custom implant is subsequently produced by first obtaining a standard investment casting wax pattern that is representative of a desired implant, and performing custom modifications by hand. This step is accomplished by a skilled craftsperson who adds wax to, or removes wax from, the standard wax pattern. This process is both labor and time intensive and it requires the expertise of a highly skilled craftsperson.

SUMMARY OF THE INVENTION

The present invention overcomes the disadvantages of manual implant fabrication by providing a precise, rapid, and flexible process for fabricating custom bioimplantable articles. The method allows complex and subtle customization, including special contoured surfaces, undercuts, internal cores, or other features, typically obtained only by post-processing machining, as well as features that cannot be machined.

In an exemplary embodiment of the invention, a method of making a custom, bioimplantable article includes the steps of creating a data file that defines a three-dimensional shape of at least a portion of the custom, bioimplantable article; providing the data file to a rapid prototyping machine; fabricating a mold representative of at least a portion of the custom, bioimplantable article with the rapid prototyping machine as defined by the data file; positioning the mold relative to an existing, non-custom representation of a bioimplantable article to define a hybrid component; creating a ceramic shell around the hybrid component; removing the existing, non-custom representation of a bioimplantable article from the ceramic shell; introducing molten metal into the ceramic shell; allowing the molten metal to harden; and removing the ceramic shell from the hardened metal.

BRIEF DESCRIPTION OF THE DRAWINGS

A more complete understanding of the present invention and the attendant advantages and features thereof will be more readily understood by reference to the following detailed description when it is considered in conjunction with the accompanying drawings wherein.

DETAILED DESCRIPTION OF THE INVENTION

Figure 1:
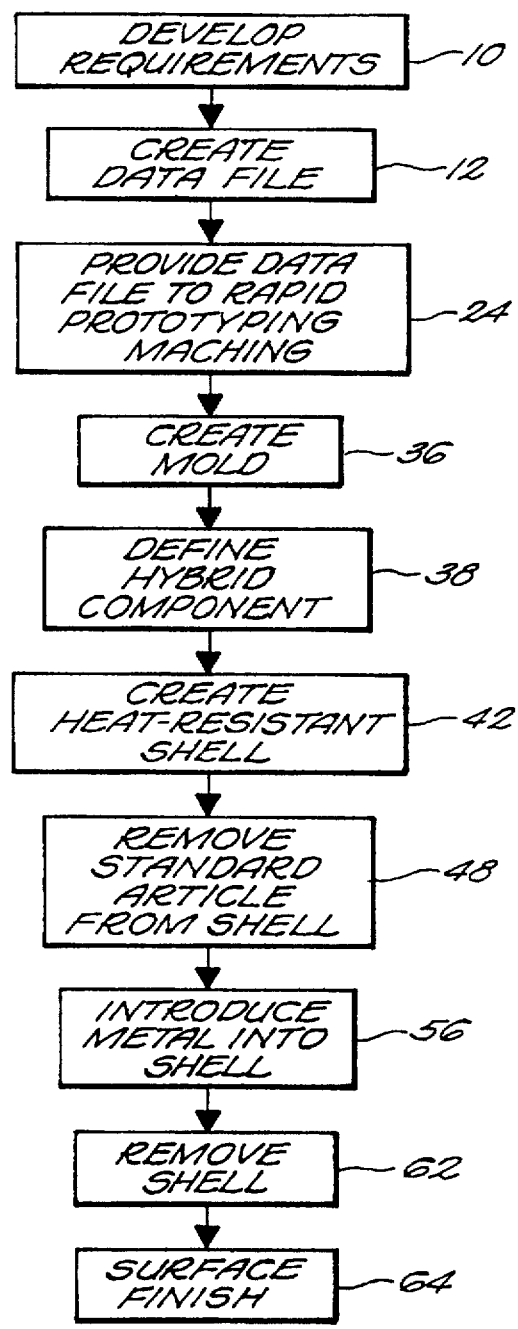
FIG. 1 is a flow chart of steps in a method of making a custom, bioimplantable article in accordance with the present invention.

FIG. 1 is a flow chart of steps in a method of making a custom, bioimplantable article in accordance with the present invention. FIGS. 2-8 illustrate various features of the steps described in FIG. 1 and should therefore be reviewed in combination with the description of FIG. 1 which follows. Additionally, as the method in accordance with the invention is suitable without modification for fabrication of any orthopedic implant, such as joint prosthesis components, the term "bioimplantable article," or simply "article" or "implant," is used in the description which follows with the intention to encompass all such implants. Accordingly, the figures are not intended to represent a particular or actual article, but are greatly simplified for the purposes of describing the method of making a custom article.

Referring now to FIG. 1, in a first step 10, an engineer or technician obtains information from a medical professional regarding an article intended for implantation. More specifically, the medical professional will identify a desired configuration for the article, which takes into account the anatomical requirements of a specific patient. Depending on the medical assessment, the implant may need modification or customization ranging from only a slight change at a particular region of the implant to an entirely altered structure. Exemplary changes include dimensional, geometrical, and textural modifications.

Figure 2:
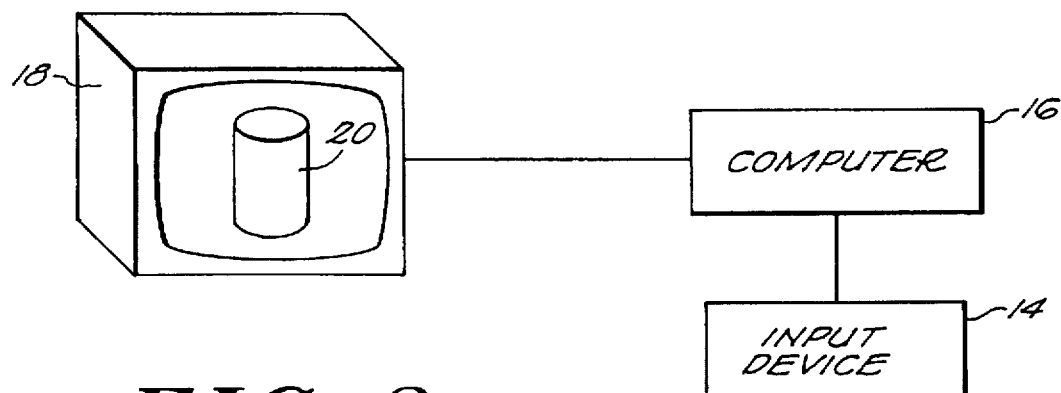
FIG. 2 is a perspective view of a three-dimensional CAD model.
Figure 3:
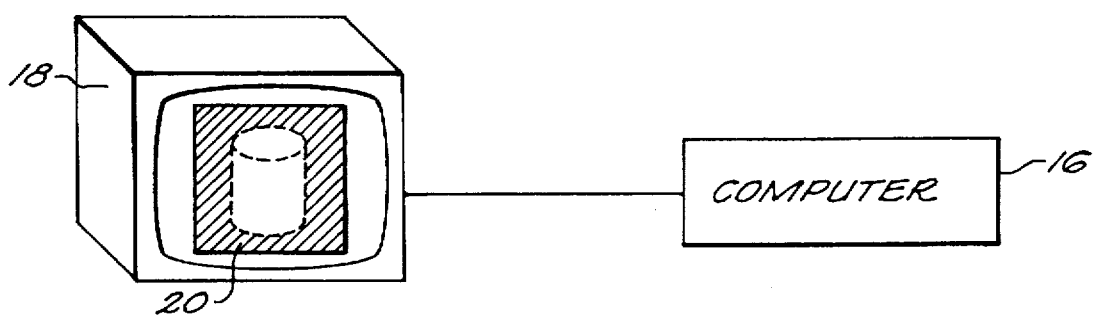
FIG. 3 is a perspective view of a shell of the three-dimensional CAD model of FIG. 2.

In a step 12, also illustrated in FIG. 2, an engineer accesses an input device 14, such as a keyboard, mouse, light pen, and the like, which is associated with a computer 16 and a display unit 18, to create a data file defining a three-dimensional article 20 representative of at least a portion of a custom, bioimplantable article. The data file can be created by any of a number of drawing, graphic, design, or solid modeling programs known to those skilled in the art. An exemplary computer aided design program (CAD) is "Pro Engineer," available from Parametric Technology Corporation. A first data set representing the article can then be manipulated by the CAD software to create a second data set representative of a negative or a shell 22 of the article 20 as illustrated in FIG. 3, to include bleeders and gates as required. Alternatively, a data set defining the shell 22 can be created without first creating a data set for the article. By initially creating the article 20 as a CAD model, the article or shell 22 can be reviewed "on screen" or as computer generated drawings by a surgeon/engineer and modified as required prior to actually creating a mold or an implant. To further improve the review and design process, a three dimensional model can be fabricated to assess potential modifications.

Figure 4:
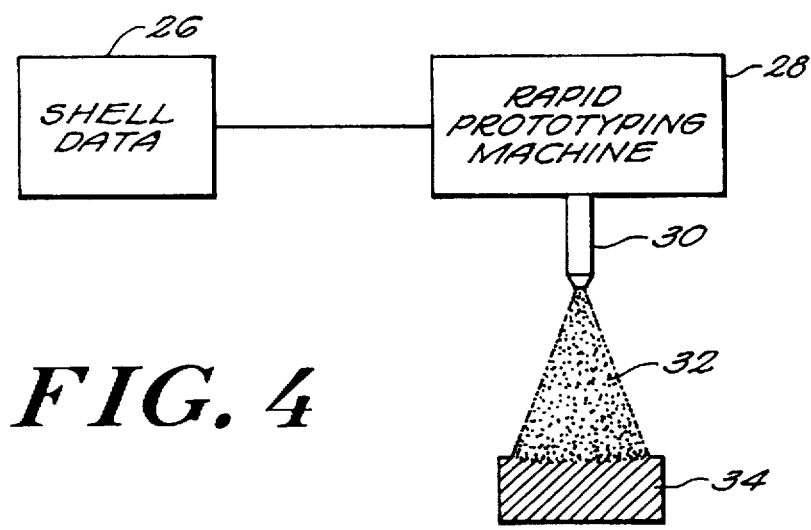
FIG. 4 is a schematic illustration of a rapid prototyping machine making a mold corresponding to the shell of FIG. 3.

In a step 24, the data file for the shell is provided to, or accessed by, a rapid prototyping machine capable of transforming the data set into a tangible object. Exemplary rapid prototyping machines include: selective laser sintering, solid ground curing, fused deposition modeling, StereoLithography, LOM, and three-dimensional printing (direct shell production). In the illustration of FIG. 4, shell data 26 is accessed by a three dimensional printer 28 manufactured by the Soligen Corporation under a license granted by the Massachusetts Institute of Technology (MIT). The three-dimensional printer 28 includes a computer controlled orifice 30 capable printing a binder 32, such as colloidal silica, on a powder bed of alumina or silica, to build-up or create an article 34 defined by the shell data 26.

In a step 36, and as shown in FIG. 4, the three-dimensional printer 28 produces a ceramic mold 34 that defines a custom portion of a bioimplantable article. When fired, and/or otherwise stabilized, loose powder removed, and post-dipped in a material that strengthens the mold for example, the mold 34 is ready for use in an investment casting process. The creation of a mold directly from a data file provides many advantages when compared to prior customization techniques. For example, many of the steps required by prior techniques are eliminated, such as crafting a custom wax model from drawings rendered by hand or from a CAD model. The reduction in steps required to make a custom mold is not only faster, but it also lessens the chance of introducing outright errors or undesirable deviations caused by tolerance stack-up. Furthermore, the complexity and subtlety of customization is greatly enhanced. Special contoured surfaces, undercuts, internal cores, or typically machined features, as well as other features that are not machineable, can be easily incorporated into the CAD model and built with the rapid prototyping machine due to its layered fabrication technique. Furthermore, subsequent modifications in configuration can be made simply and quickly by modifying the CAD model and rebuilding the article with the rapid prototyping machine.

Figure 5:
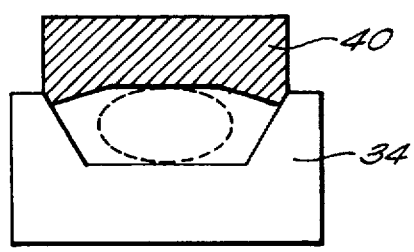
FIG. 5 is a simplified perspective view of the mold of FIG. 4 associated with a non-custom representation of a bioimplantable article.

In a step 38, illustrated in FIG. 5, a single, non-custom representation of a bioimplantable article 40 is selected from a supply of articles, that have characteristics desirable for combining with a mold 34 for a custom implant portion, to create a hybrid mold for investment casting that includes both custom and standard features. For example, a wax or plastic pattern of a standard sized knee femoral component can be selected for association with a custom portion shaped to bridge between the femoral component and the remaining bone surfaces on the femur. The custom section could include special holes for stem and screw placement to aid a surgeon to securely place the implant.

Continuing to refer to FIG. 5, a hybrid component configuration can be defined by placing the non-custom article 40 in, on, near, or apart from the custom mold 34. The article 40 can be secured to the mold 34 with an adhesive material or a grout such as a refractory cement, and any gaps or spaces between the article 40 and the mold 34 can be filled with wax or refractory cement as desired to create additional mold boundaries or gates.

Figure 6:
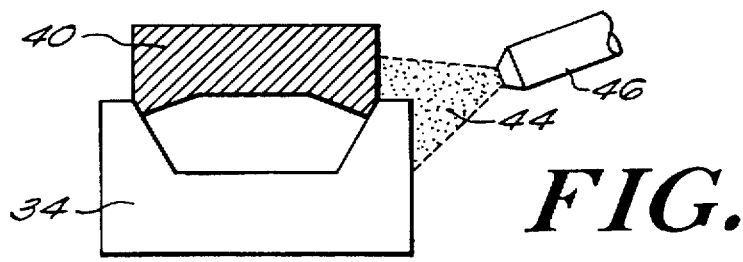
FIG. 6 is an illustration of a ceramic shell being created around the hybrid component of FIG. 5.
Figure 7:
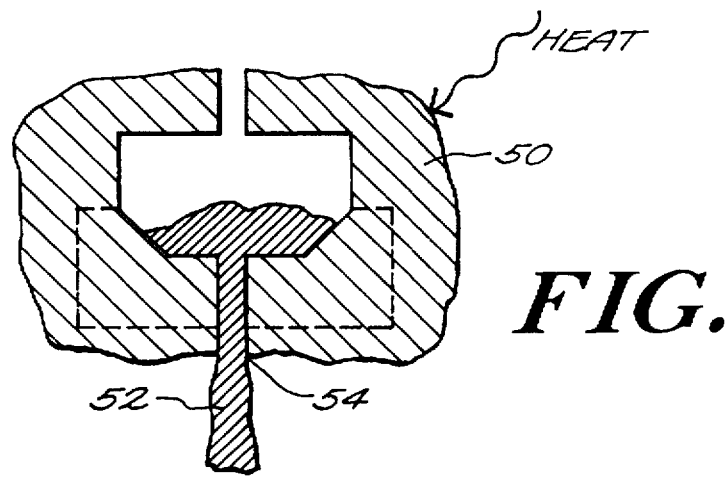
FIG. 7 illustrates removal of the non-custom representation of a bioimplantable article from the ceramic shell.
Figure 8:
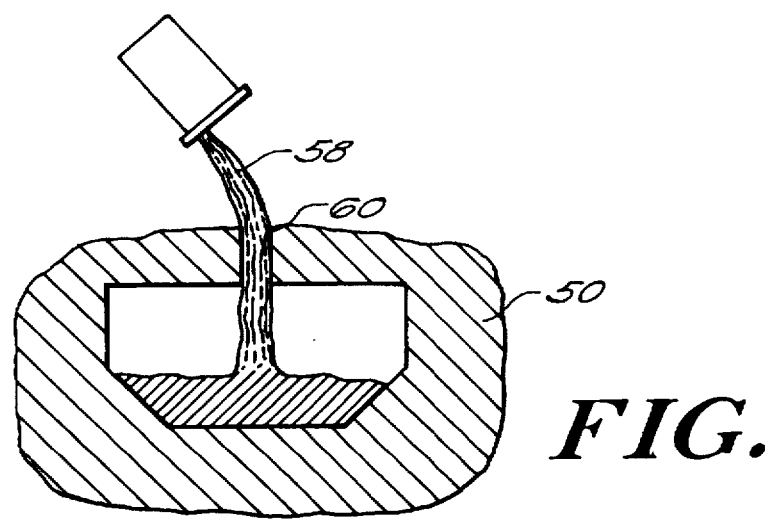
FIG. 8 illustrates molten metal being introduced into the ceramic shell.

In a step 42, depicted in FIG. 6, the associated custom mold 34 and standard article 40 are coated with particles 44 of a refractory material that can be ejected from a nozzle 46 to create a shell that becomes a single mold. The ceramic can also be applied by spreading a ceramic paste with a tool, dipping, or by other techniques known to those skilled in the art. The gates or openings that were defined during CAD modeling are not covered with ceramic. In a step 48, illustrated in FIG. 7, the standard article 40 is removed from the ceramic shell 50 with the application of heat. Typically, the shell 50 is heated until the article 40 melts, burns, or vaporizes. The liquid, ash or vapor 52 is then drained or exhausted from one or more bleeders or gates 54.

The subsequent steps of the method are not discussed in great detail as they are well known to those skilled in the art of metal casting. In a step 56, illustrated in FIG. 8, molten metal 58 is introduced into the ceramic shell 50 through a gating system 60. An exemplary metal suitable for biomedical implantation is Co-Cr-Mo alloy (ASTM F75). The shell and metal are allowed to cool and, in a step 62, the shell is removed from the hardened metal. In a step 64, the custom implant is subjected to post-machining, grinding off the gates, bead blasting, and polishing, as required.

Although the invention has been shown and described with respect to exemplary embodiments thereof, various other changes, omissions and additions in form and detail thereof may be made therein without departing from the spirit and scope of the invention.

What is claimed is:

1. A method of making a custom, bioimplantable article comprising the steps of:

creating a data file that defines a three-dimensional shape of at least a portion of the custom, bioimplantable article;

providing the data file to a rapid prototyping machine;

fabricating a mold representative of at least a portion of the custom, bioimplantable article with the rapid prototyping machine as defined by the data file;

positioning the mold relative to an existing, non-custom representation of a bioimplantable article to define a hybrid component;

creating a ceramic shell around the hybrid component;

removing the existing, non-custom representation of a bioimplantable article from the ceramic shell;

introducing molten metal into the ceramic shell;

allowing the molten metal to harden; and removing the ceramic shell from the hardened metal.

2. The method of claim 1, wherein the data file is created with a computer aided design program, and wherein the step of creating a data file includes the steps of:

creating a first data set that defines a three dimensional article; and manipulating the first data set to create a second data set that defines a shell of the three dimensional article.

3. The method of claim 1, wherein the data file is created with a computer aided design program, and wherein the step of creating a data file includes the step of creating a data set that defines a mold for a three dimensional article.

4. The method of claim 1, wherein the custom, bioimplantable article is a joint prosthesis component.

5. The method of claim 1, wherein the rapid prototyping machine performs three dimensional printing.

6. The method of claim 1, wherein the step of fabricating a mold with the rapid prototyping machine includes the step of building-up a ceramic shell having a configuration that is substantially identical to the shell of the custom implant created with the computer aided design program.

7. The method of claim 1, wherein the step of positioning the mold includes the steps of:

juxtaposing the existing, non-custom representation of a bioimplantable article with the mold; and attaching the existing, non-custom representation of a bioimplantable article to the mold with refractory cement.

8. The method of claim 7, further comprising the step of filling voids between the mold and the existing, non-custom representation of a bioimplantable article with wax.

9. The method of claim 7, further comprising the step of filling voids between the mold and the existing, non-custom representation of a bioimplantable article with refractory cement.

10. The method of claim 1, further comprising the step defining gates in the data file.

11. The method of claim 1, wherein the step of removing the existing, non-custom representation of a bioimplantable article from the ceramic shell includes the steps of:

heating the existing, non-custom representation of a bioimplantable article to a molten state; and allowing the molten article to flow out of the ceramic shell.

12. The method of claim 1, wherein the step of removing the existing, non-custom, bioimplantable article from the ceramic shell includes the steps of:

combusting the existing, non-custom representative of a bioimplantable article to a vapor state; and exhausting the vaporized article from the ceramic shell.

13. A method of making a custom joint prosthesis component comprising the steps of:

creating a data file with a computer aided design program that defines a three-dimensional shape of at least a portion of the custom joint prosthesis component;

providing a rapid prototyping apparatus;

providing the data file to the rapid prototyping machine;

fabricating a mold for at least a portion of the custom joint prosthesis component with the rapid prototyping machine by forming a ceramic shell as defined by the data file;

providing a plurality of non-custom representations of a biomedical article;

selecting one of the non-custom representations of the biomedical article;

juxtaposing the selected, non-custom representation of a biomedical article with the mold;

attaching the selected, non-custom representation of a biomedical article to the mold with refractory cement to define a hybrid component;

creating a ceramic shell around the hybrid component;

removing the selected, non-custom representation of a biomedical article from the ceramic shell by heating the selected, non-custom representation of a biomedical article to a molten state; and allowing the molten article to flow out of the ceramic shell;

introducing molten metal into the ceramic shell;

allowing the molten metal to harden; and removing the ceramic shell from the hardened metal.

14. The method of claim 13, wherein the data file is created with a computer aided design program, and wherein the step of creating a data file includes the steps of:

creating a first data set that defines a three dimensional article; and manipulating the first data set to create a second data set that defines a shell of the three dimensional article.

15. The method of claim 13, wherein the data file is created with a computer aided design program, and wherein the step of creating a data file includes the step of creating a data set that defines a mold for a three dimensional article.

16. The method of claim 13, wherein the rapid prototyping machine performs three dimensional printing.

17. The method of claim 13, wherein the non-custom representations of a biomedical article consist of wax patterns.

18. The method of claim 13, wherein the non-custom representations of a biomedical article consist of plastic patterns.

19. A method of making a custom orthopedic implant comprising the steps of:

creating a custom orthopedic implant model using computer aided design techniques;

creating a shell of the orthopedic implant model using computer aided design techniques;

forming a ceramic mold representative of the shell of the orthopedic implant model with a rapid prototyping machine;

providing a heat destructible implant model;

juxtaposing the heat destructible implant model with the ceramic mold to provide a hybrid component;

creating a ceramic shell around the hybrid component;

applying heat to the ceramic shell to destroy the heat destructible implant model;

introducing molten metal into the ceramic shell;

allowing the molten metal to harden; and removing the ceramic shell from the hardened metal.

* * * * *